US010350200B2

(12) United States Patent
Dixon et al.

(10) Patent No.: US 10,350,200 B2
(45) Date of Patent: Jul. 16, 2019

(54) AQUEOUS SUSPENSIONS OF OXIMES FOR AUTOINJECTORS

(71) Applicant: Southwest Research Institute, San Antonio, TX (US)

(72) Inventors: Hong Dixon, Helotes, TX (US); Joseph A. McDonough, Helotes, TX (US); Larry A. Cabell, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 15/412,622

(22) Filed: Jan. 23, 2017

(65) Prior Publication Data

US 2018/0207143 A1    Jul. 26, 2018

(51) Int. Cl.
*A61K 31/44* (2006.01)
*A61K 31/439* (2006.01)
*A61M 5/32* (2006.01)
*A61M 5/20* (2006.01)
*A61M 5/315* (2006.01)

(52) U.S. Cl.
CPC ............ *A61K 31/44* (2013.01); *A61K 31/439* (2013.01); *A61M 5/20* (2013.01); *A61M 5/3157* (2013.01); *A61M 5/32* (2013.01); *A61M 5/3287* (2013.01); *A61M 2005/2026* (2013.01)

(58) Field of Classification Search
None
See application file for complete search history.

(56) References Cited

U.S. PATENT DOCUMENTS

| | | | |
|---|---|---|---|
| 3,043,675 A | 7/1962 | Steinhards et al. | |
| 3,468,896 A | 9/1969 | Myers et al. | |
| 3,629,425 A * | 12/1971 | Hussain | A61K 31/44 514/357 |
| 6,495,164 B1 * | 12/2002 | Ramstack | A61K 9/0019 424/484 |
| 8,404,850 B2 | 3/2013 | Cabell et al. | |
| 8,722,706 B2 * | 5/2014 | Dixon | A61K 9/0019 514/332 |
| 9,028,873 B2 | 5/2015 | McDonough et al. | |
| 2007/0093518 A1 | 4/2007 | Wetherell et al. | |
| 2010/0040692 A1 | 2/2010 | Dixin et al. | |
| 2011/0195125 A1 | 8/2011 | McDonough et al. | |
| 2014/0249140 A1 | 9/2014 | Niquet et al. | |
| 2014/0323473 A1 * | 10/2014 | Quinn | C07D 213/64 514/221 |
| 2015/0313868 A1 * | 11/2015 | Morgan | A61K 31/352 514/221 |

FOREIGN PATENT DOCUMENTS

| | | | |
|---|---|---|---|
| CA | 689384 A * | 6/1964 | |
| CA | 689384 A | 6/1964 | |
| GB | 1 397 722 | 6/1975 | |
| WO | WO 2014179228 A1 * | 11/2014 | ............ A61M 11/02 |

OTHER PUBLICATIONS

The Product Description of Pralidoxime Chloride Injection from Meridian Medical Technologies (downloaded Aug. 25, 2017 from: https://dailymed.nlm.nih.gov/dailymed/archives/fdaDrugInfo.cfm?archiveid=2520.*
G.A. Petroianu, S. M. Nurulain, N. Nagelkerke, M. A. H. Al-Sultan, K. Kuça and J. Kassa. Five oximes (K-27, K-33, K-48, BI-6 and methoxime) in comparison with pralidoxime: survival in rats exposed to the organophosphate paraoxon. J. Appl. Toxicol. 2006; 26: 262-268.*
Karl E. Friedl, Charles J. Hannan Jr ., Paul w. Schadler and Willis H. Jacob. Journal of Pharmaceutical Sciences, vol. 78, No. 9, pp. 728-731, 1989. (Year: 1989).*
S. Ogston-Tuck, Intramuscular injection technique: an evidence-based approach. Nursing Standard, 29, 4, 52-59, 2014. (Year: 2014).*
Robert I. Ellin. "Stability of Concentrated Aqueous Solutions of Pralidoxime Chloride." Journal of Pharmaceutical Sciences vol. 71, No. 9, Sep. 1982, pp. 1057-1059 (Year: 1982).*
Choi, B. S., et al: "Stabilizing NaCl Particles with Cd2+ in a Saturated Solution During ex situ PSD Measurement"; Journal of Crystal Growth 269, May 23, 2004 (9 pgs).
Clark, A. P.-Z, et al: "Good Manufacturing Practice: Manufacturing of a Nerve Agent Antidote Nanoparticle Suspension"; International Journal of Toxicology 32 (Supplement 2), 2013, (pp. 5S-17S).
Clark A. P.-Z, et al: "Non-Newtonian Suspension Formulations for Improved Stability and Delivery of Autoinjectable CBRN Countermeasures"; Military Medical Science Letters 2014, vol. 83, Apr. 7, 2014, pp. 18-27.
Dixon, H., et al; "MMB4 DMS Nanoparticle Suspension Formulation With Enhanced Stability for the Treatment of Nerve Agent Intoxication"; International Journal of Toxicology 32 (Supplement 2), 2013, pp. 18S-29S.
Friedl, K. E., et al; "Atropine Absorption after Intramuscular Administration with 2-Pralidoxime Chloride by Two Automatic Injector Devices"; Journal of Pharmaceutical Sciences, vol. 78, No. 9, Sep. 1989, pp. 728-731.
Grosev, V.M., et al; "Vibrational Analysis of 1-methyl-pyridinium-2-aldoxime and 1-methyl-pyridinium-4-aldoxime cations"; Spectrochimica ACTA Part A: Molecular & Biomolecular Spectroscopy, vol. 78A, Issue 5, May 2011, pp. 1376-1379.
Hoffman, M.D., R.S., et al; "Preparing for Chemical Terrorism: A Study of the Stability of Expired Pralidoxime (2-PAM)", Disaster Medicine and Public Health Preparedness, vol. 6, No. 1, 2012, pp. 20-25, American Medical Association, USA.
Jain, N., et al; "Development and Evaluation of Combined Drug Formulation for Autoject-injector, for Emergency Application in Organophosphate Poisoning"; Defence Science Journal vol. 62, No. 2, Mar. 13, 2012, pp. 105-111.

(Continued)

*Primary Examiner* — Michael P Cohen

(74) *Attorney, Agent, or Firm* — Grossman, Tucker et al

(57) ABSTRACT

The present invention is directed at aqueous suspensions of oxime compounds, such as 2-pyridine aldoxime methyl chloride (2-PAM Cl) for autoinjectors. The suspensions are able to provide 600 mg of 2-PAM Cl in one relatively small dose of less than or equal to 1.0 mL, and are particularly useful for placement in relatively small size autoinjectors.

10 Claims, 1 Drawing Sheet

(56) References Cited

OTHER PUBLICATIONS

John, H., et al; "Review of UV Spectroscopic, Chromatographic, and Electrophoretic Methods for the Cholinesterase Reactivating Antidote Pralidoxime (2-PAM)", Drug Test Analysis, vol. 4, 2012, pp. 179-193.

Kumar, P., et al: "Shelf Life Studies of Pralidoxime Chloride Solution in Autoinjector Cartridges Stored at Room Temperature"; Current Trends in Biotechnology and Pharmacy vol. 2, 2008, (9 pgs).

Mcalister, PhD, D.R.; "Gamma Ray Attenuation Properties of Common Shielding Materials", Jan. 3, 2013, (14 pgs); PG Research Foundation Inc., Lisle Illinois USA.

Mullany, L.C., et al; "Cumulative Effects of Heat Exposure and Storage Conditions of Oxytocin-in-Uniject in Rural Ghana: Implications for Scale Up"; Global Health: Science and Practice vol. 2, No. 3, 2014, pp. 285-294.

O'Donnell, K.; "Mean Kinetic Temperature Storage vs. Shipping and the Vagaries of Regulatory Requirements"; Contract Pharma Times, Advanced Degrees, Jul./Aug. 2008, vol. 40, No. 10 (pp. 26-28).

Sidell, M.D., F.R.; Modification by Diluents of Effects of Intramuscular Atropine on Heart Rate in Man; Clinical Pharmacology and Therapeutics, May 21, 1974, vol. 16, No. 4 (pp. 711-715).

Smith, P.E.; "The Effect of Urea on the Morphology of NaCl Crystals: A Combined Theoretical and Simulation Study"; (author manuscript), National Institutes of Health Public Access, Fluid Phase Equilibrium (final edited published form), Mar. 25, 2010; , 290(1-2): pp. 36-42.

Svendsen, O., et al; "Intramuscular Injection of Hypertonic Saline: In vitro and in vivo Muscle Tissue Toxicity and Spinal Neurone c-fos Expression"; Basic & Clinical Pharmacology & Toxicology, 2005, vol. 97 (pp. 52-57).

VanHavre, W., et al; 2-[(Hydroxyimino)methyl]-1-methylpyridinium Chloride, ACTA Cryst. B38, 1982, pp. 2516-2518.

Vijayaraghavan, R.; "Autoinjector Device for Rapid Administration of Live Saving Drugs in Emergency Situations,"; Defence Science Journal, vol. 62, No. 5, Sep. 2012 ( pp. 307-314).

Zand, R.Z., et al; "The Corrosion Resistance of 316L Stainless Steel Coated With a Silane Hybrid Nanocomposite Coating"; Progress in Organic Coatings, Vo. 72, Aug. 2011, pp. 709-715.

Nikipedia, Cottonseed Oil, <<https://en.wikipedia.org/wiki/Cottonseed_oil>> (accessed Feb. 7, 2017).

BD Pharmaceuticals; "Auto-Disable Injection System"; <<http://www.bd.com/pharmaceuticals/products/auto-disable.asp>> (accessed Feb. 7, 2017).

PATH: Uniject Injection System; "The Radically Simple Uniject™ Injection System Rethinking the Needle to Extend the Reach of Contraception, Medicines, and Vaccines"; <<http://www.path.org/projects/uniject.php >> (accessed Feb. 2, 2017—9 pgs).

VAISALA/ Application Note, Cold Chain Compliance; "USP Guidance Chapters for Temperature-Controlled Supply Chains" <<http://www.vaisala.com/Vaisala%20Documents/Application%20notes/Application%20Note_Cold%20Chain%20Compliance%20USP.pdf>>; (accessed Feb. 7, 2017, 2 pgs).

* cited by examiner

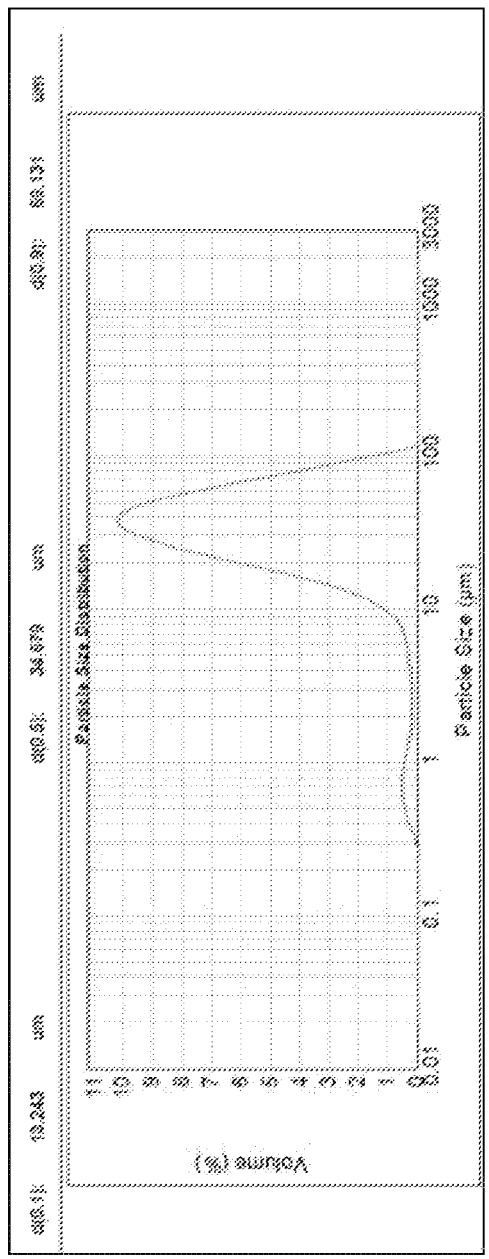

AQUEOUS SUSPENSIONS OF OXIMES FOR AUTOINJECTORS

FIELD

The present invention is directed at aqueous suspensions of oxime compounds, such as 2-pyridine aldoxime methyl chloride (2-PAM Cl) for autoinjectors. The suspensions are able to provide 600 mg of 2-PAM Cl in one relatively small dose of less than or equal to 1.0 mL, and are particularly useful for placement in relatively small size autoinjectors.

BACKGROUND

Organophosphate (OP) nerve agents represent a threat to military personnel and civilians. In order to avoid a cholinergic crisis due to permanent binding of the nerve agent to acetylcholinesterase (ACHE) and the accumulation of acetylcholine (Ach) in the synaptic cleft, a reactivator such as 2-pyridine aldoxime methyl chloride (2-PAM Cl) must be delivered to debind the organophosphate from the enzyme within minutes of exposure. In addition, effective treatment may involve the delivery of another active pharmaceutical ingredient (API), such as a competitive inhibitor (e.g., atropine sulfate-ATR) of the muscarinic receptor, antagonizing the action of excess Ach. 2PAM CL and ATR may therefore provide a synergistic effect when injected in rapid succession.

Since such drugs must be delivered within minutes of OP exposure, autoinjectors are preferred. An autoinjector may be understood herein as a medical device designed to deliver a dose of a particular drug and typical autoinjectors are spring-loaded syringes which are intended for self-administration by a patient. Commercially available autoinjectors can deliver, e.g., 2 mL, 1 mL and 0.7 mL of liquid.

Reference is made to Canadian Patent Application No. 689384 entitled "Method For Producing 2-Pyridinealdoxime Methochloride." A method of preparation of 2-pyridinealdoxime methochloride is disclosed and it is reported that such compound occurs as a white crystalline powder which is soluble in water to the extent of one gram in less than one cc.

Accordingly, a need remains for a relatively stable aqueous suspension of oxime compounds, optionally combined with another API, suitable for treatment of exposure to OP nerve agents. More specifically a need remains for aqueous suspensions of oximes which can provide one dose of 600 mg of the oxime compound in aqueous suspension contained in a 1.0 mL or smaller autoinjector device, along with requisite shelf-life stability.

SUMMARY

In a first exemplar embodiment, the present disclosure is directed at an aqueous formulation comprising an oxime in water. The oxime is present at a level of at least about 600 mg and the amount of water is in the range of about 205 mg to about 550 mg, wherein the volume of the formulation is in the range of 0.7 cc to 1.0 cc.

In related embodiment, the present disclosure relates to an autoinjector having an injection volume of 0.7 cc to 1.0 cc including a needle at a 21-24 gauge size, where the autoinjector is configured to deliver a dose of an aqueous formulation upon actuation by an individual. The aqueous formulation within the autoinjector comprises an oxime in water wherein the oxime is present at a level of at least about 600 mg and the amount of water is in the range of about 205 mg to about 550 mg, wherein the volume of the formulation is in the range of 0.7 cc to 1.0 cc.

FIGURES

The followed detailed description of various preferred embodiments of the present disclosure will be better understood when read in conjunction with the appended drawings, a brief summary of which is provided below:

FIG. 1 illustrates the particle size distribution of 2-pyridine aldoxime methyl chloride.

DETAILED DESCRIPTION

The present disclosure is directed at aqueous suspensions of oxime compounds, optionally combined with another active pharmaceutical ingredient (API), which can be used as antidotes for nerve agent exposure in selected size autoinjectors. A nerve agent is reference to a compound that inactivates aceythylcholinesterase by phosphorylation of the molecule. Oxime compounds can reactivate acetylcholinesterase by attaching to the phosphorous atom and forming an oxime-phosphonate, which then splits away from the acetylcholinesterase molecular. The oxime compounds preferably for use herein include 2-pyridine aldoxime methyl chloride (2-PAM Cl) which has the following general structure:

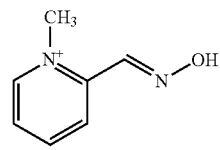

The 2-PAM Cl is available from Dishman Pharmaceuticals. The 2-PAM Cl was then milled to a particle size distribution as illustrated in FIG. 1. Preferably, such milling may be accomplished with a hammer mill, such as a FitzMill L1A. As can be seen, the particle size distribution preferably includes particles having a size in the range of 10.0 μm to 100.0 μm. The average (mean) particle size is preferably in the range of 30.0 μm to 50.0 μm, more preferably the average particle size is 40.0 μm, +/−10.0 μm.

Other oximes contemplated for use herein include bisquaternary pyridinium-2-aldoxime salt of the formula:

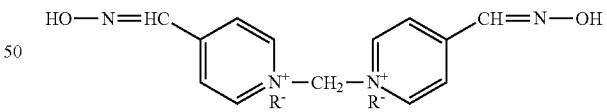

where R⁻ refers to an anionic counterion and which may comprise a halide (Cl⁻ or Br⁻ or I⁻).

In addition the bispyridinium oximes contemplated for use herein include one or more of the following:

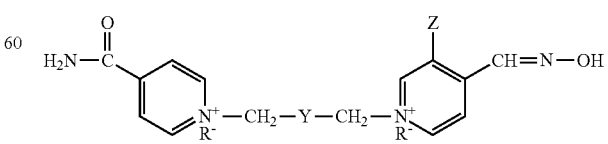

wherein in the above formula, when Y is O and Z is H and where R may be a chloride anion (Cl⁻) the molecule is known as HI6-Cl or 1-(2-hydroxyiminomethyl) pyridinium)-3-(4-carbamoylpyridinium)-2-oxapropane dichloride) and where R is a methane sulphonate anion (CH$_3$SO$_3^-$) the molecule is known as HI6 DMS or 1-(2-(hydroxyiminomethyl) pyridinium)-3-(4-carbamoylpyridinium)-2-oxapropane dimethanesulphonate. When Y is O and Z is —CHNHOH and the R$^-$ groups amount to an iodide anion (I$^-$) the molecule is known as HLo7 or [(Z)-[1-[4-carbamoylpyridin-1yl)methoxymethyl]-2-[(Z)-hydroxyiminomethyl]pyridine-4-ylidene]methyl]-oxo-azanium diiodide.

As noted, optionally, one may include a relative small amount of API in the aqueous suspension to block the action of acetylcholine at muscarinic receptors. One preferred API includes atropine sulfate or scopolamine. Preferably, the level of such APIs is such that 1-10 mg is provided in the suspension of the 2-PAM Cl, which level has been found not to significantly influence the rheology of the suspension for administration purposes.

The 2-PAM Cl having the above reference particle size distribution was placed in water at ambient temperature. It was first identified that such 2-PAM Cl having the indicated particle size distribution provided that 352 mg of the 2-PAM Cl would dissolve in 648 mg of water. Next, 780 mg of 2-PAM Cl was placed in a 220 mg of water. It was determined that in this situation, the amount of 2-PMA Cl that dissolved was: 220 mg H$_2$O×(352 mg 2-PAM Cl/648 mg H$_2$O)=120 mg. Accordingly, when 780 mg of 2-PMA Cl herein is placed in 220 mg of water, 120 mg will dissolve, and 660 mg will be as solid in suspension. It can also then be appreciated that if 120 mg of 2-PAM Cl herein dissolved in 220 mg of water, then the amount of 2-PAM Cl herein that will dissolve in 1 gram of water will be: 1000 mg H$_2$O×(120 mg 2-PAM Cl/220 mg H$_2$O)=545 mg 2-PAM Cl.

From the above, it may now be appreciated that with respect to the use of a 1.0 ml autoinjector, such volume may now be utilized to provide a requisite does of 2-PAM Cl of at least 600 mg. More specifically, with a 1.0 ml volume restriction, and with the goal of supplying 600 mg of 2-PAM Cl, it is first noted that maximum solubility of a 2-PAM Cl/water solution prepared herein with the 2-PAM Cl at the identified particle size distribution, indicated a density of about 1.15 g/cc. Accordingly, with a goal of about 600 mg for delivery, it can be estimated that 1.0 ml will weigh 1150 mg. Therefore, about 600 mg of 2-PAM Cl herein can now be combined with about 550 mg of water and be introduced into a 1.0 ml autoinjector for delivery of the requisite amount of 2-PAM Cl upon nerve agent exposure. It can be appreciated that reference to "about" in the foregoing is reference to the feature that the amount of 2-PAM Cl as well as the amount of water may vary about +/−10 mg.

Expanding on the above, with respect to a 0.7 ml size autoinjector, such may now be utilized to provide a requisite does of 2-PAM Cl of 600 mg. More specifically, with a 0.7 ml volume restriction, and with the goal of supplying 600 mg of 2-PAM Cl, it is first noted that maximum solubility of a 2-PAM Cl/water solution prepared herein with the 2-PAM Cl at the identified particle size distribution, again indicated a density of about 1.15 g/cc. Accordingly, with a goal of 600 mg for delivery, it can be estimated that 0.7 ml will weigh 805 mg (0.7 ml×1.15 g/cc). Therefore, about 600 mg of 2-PAM Cl herein can now be combined with about 205 mg of water and be introduced into a 0.7 ml autoinjector for delivery of the requisite amount of 2-PAM Cl upon nerve agent exposure. It can be appreciated that once again, reference to "about" in the foregoing is reference to the feature that the amount of 2-PAM Cl as well as the amount of water may vary about +/−10 mg.

It may therefore now be appreciated that in the broad context of the present disclosure, one may combine an oxime with water, wherein the oxime, preferably 2-PAM Cl, is present at a level of at least about 600 mg and the amount of water may be in the range of about 205 mg to about 550 mg, wherein the volume of the formulation is between 0.7 cc to 1.0 cc. Accordingly, at least 600 mg of the oxime, preferably 2-PAM Cl, may be delivered via use of autoinjectors having a 0.7 cc or 1.0 cc volume limitation. Once again, reference to "about" in the foregoing is reference to the feature that the amount of 2-PAM Cl as well as the amount of water may vary about +/−10 mg.

In addition to now being capable of providing the requisite dose of 600 mg of 2-PAM Cl in either a 1.0 ml or 0.7 ml autoinjector, it should be noted that such autoinjectors are preferably configured herein to include the use of 21-24 gauge needles. It is noted that a 21 gauge needle will have a nominal inner diameter of 0.51 mm. A 22 gauge needle as used herein will have a nominal inner diameter of 0.41 mm. A 23 gauge needle as used herein will have a nominal inner diameter of 0.34 mm and a 24 gauge needle has a nominal inner diameter of 0.31 mm. In particular preferred embodiments, the needle gauge is 21-22 gauge. It is contemplated herein that the oxime compound suspension is such that the particle size distribution in the preferred range of 10.0 μm to 100.0 μm is such that it will not increase in size during storage to trigger clogging of the identified needle diameters.

It should be noted that reference to an autoinjector herein may be understood as an injector device that, upon actuation (e.g., pressing of a button), a syringe needle is automatically inserted and the subject drug is delivered at a selected dose. Typically, the autoinjector is a spring loaded device. Preferably, once the injection is complete the autoinjectors may provide an indication to the user to confirm that a particular dose has been delivered. In such context, autoinjectors herein may include gas jet autoinjectors which contain a cylinder of pressurized gas that propels a jet of the liquid dose through the skin without the use of a needle. As noted, the autoinjectors that are preferred for use herein are those that include 0.7 ml and 1.0 ml volume capability.

In addition, to the above, the autoinjector volume herein may include other optional components, in relatively small amounts, such as 1-50 mg of other excipients (inert ingredients with respect to drug activity). Such excipients may therefore be incorporated to improve the flow of the oxime/water mixture, as well as its stability, when used in an autoinjector. Preferably, such excipients can include polyethylene glycol sorbitan monooleate (Tween 80) and polyethylene glycol 400 (polyethylene glycol with a MW in the range of 380-420 g/mol).

The formulation herein for use in the aforementioned 0.7 ml or 1.0 ml autoinjectors have been found to remain stable over the temperature range of −20° C. to 70° C., meaning that the formulations upon delivery were seen to maintain their desired therapeutic effect. Reference is made to the particular examples below illustrating this stability profile:

Example 1

To a vial, 4.3104 g 2-PAM Cl and 1.1942 g of deionized water was mixed which resulted in a flowable white colored suspension. The formulation was loaded into a 5.0 ml vial and was easily injected through a 21 or 22 gauge needle. The formulation was then placed inside a freezer for about 24 hours, and after thawing at room temperature, the sample remained visibly unchanged and was still easily injected through the needles noted above.

Example 2

To a vial, 4.3020 g of 2-PAM Cl and 1.2173 g of dionized water was mixed which resulted in flowable white colored suspension. The formulation was divided into three vials and stored at 40° C., 60° C. and 70° C. for three (3) days. At the end of such testing, all three samples remained visibly unchanged.

It has also been recognized herein that the aqueous formulations herein can be sterilized by radiation (gamma or E-beam), gas sterilization (ethylene oxide) or steam. The aqueous formulations of the 2-PAM Cl in water were evaluated at 121° C./15 psi, 15 min, the condition that kills bacterial spores. It was determined that: (1) 2-PAM Cl was chemically stable in the 780 mg/g aqueous suspension formulation after steam sterilization, at 97% of pre-sterilization level; and (2) the aqueous 2-PMA Cl formulation appeared to be physically stable—the sample appearance remained the same before and after steam sterilization.

While the invention herein has been disclosed with reference to various specific embodiments, it is apparent that other embodiments and variations may be devised by those skilled in the art.

What is claimed is:

1. An aqueous formulation comprising a mixture of:
   2-pyridine aldoxime methyl chloride at an average particle size in the range of 30.0 μm to 50.0 μm present at a level of at least about 600 mg; and
   water in the range of about 205 mg to about 550 mg, wherein the volume of the formulation is in the range of 0.7 cc to 1.0 cc,
   wherein said formulation remains stable over a temperature range of −20° C. to 70° C.

2. The aqueous formulation of claim 1 further containing 1-10 mg of a second active pharmaceutical ingredient.

3. The aqueous formulation of claim 2 wherein the active pharmaceutical ingredient comprises atropine sulfate or scopolamine.

4. The aqueous formulation of claim 1 including 1-50 mg of an excipient.

5. The aqueous formulation of claim 4 wherein the excipient comprises polyethylene glycol sorbitan monooleate or polyethylene glycol 400.

6. An autoinjector comprising:
   an injection volume of 0.7 cc to 1.0 cc and having a needle at a 21-24 gauge size, said autoinjector configured to deliver a dose of an aqueous formulation upon actuation by an individual;
   said aqueous formulation comprising 2-pyridine aldoxime methyl chloride in water, wherein said 2-pyridine aldoxime methyl chloride at a particle size of 30.0 μm to 50.0 μm is present at a level of at least about 600 mg and the amount of water is in the range of about 205 mg to about 550 mg,
   wherein the volume of the formulation is in the range of 0.7 cc to 1.0 cc, and
   wherein said formulation remains stable over a temperature range of −20° C. to 70° C.

7. The autoinjector of claim 6 wherein the aqueous formulation further contains 1-10 mg of an active pharmaceutical ingredient.

8. The autoinjector of claim 7 wherein the active pharmaceutical ingredient comprises atropine sulfate or scopolamine.

9. The autoinjector of claim 6 wherein the aqueous formulation includes 1-50 mg of an excipient.

10. The autoinjector of claim 9 wherein the excipient comprises polyethylene glycol sorbitan monooleate or polyethylene glycol 400.

* * * * *